(12) United States Patent
VanMeter, Jr.

(10) Patent No.: US 9,629,639 B2
(45) Date of Patent: Apr. 25, 2017

(54) ARRANGEMENT FOR SECURING INSTRUMENT TO BONE

(75) Inventor: J. Brock VanMeter, Jr., Leesburg, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 2706 days.

(21) Appl. No.: 11/895,840

(22) Filed: Aug. 28, 2007

(65) Prior Publication Data

US 2009/0062801 A1    Mar. 5, 2009

(51) Int. Cl.
| | | |
|---|---|---|
| *A61F 5/00* | (2006.01) | |
| *A61B 17/15* | (2006.01) | |
| *A61B 17/17* | (2006.01) | |
| *A61B 17/86* | (2006.01) | |
| *A61B 17/88* | (2006.01) | |
| *A61B 90/00* | (2016.01) | |

(52) U.S. Cl.
CPC .......... *A61B 17/155* (2013.01); *A61B 17/157* (2013.01); *A61B 17/1764* (2013.01); *A61B 17/86* (2013.01); *A61B 17/8875* (2013.01); *A61B 2090/034* (2016.02)

(58) Field of Classification Search
USPC ........ 606/86, 96, 98, 914–916, 86 R–89, 99, 606/104
See application file for complete search history.

(56) References Cited

U.S. PATENT DOCUMENTS

| | | | |
|---|---|---|---|
| 5,445,642 A | | 8/1995 | McNulty et al. |
| 5,688,279 A | | 11/1997 | McNulty et al. |
| 5,709,689 A | | 1/1998 | Ferrante et al. |
| 5,910,143 A | * | 6/1999 | Cripe et al. ..................... 606/87 |
| 5,925,049 A | | 7/1999 | Gustilo et al. |
| 6,096,043 A | | 8/2000 | Techiera et al. |
| 6,758,850 B2 | | 7/2004 | Smith et al. |
| 2003/0191472 A1 | * | 10/2003 | Michelson ..................... 606/61 |

(Continued)

FOREIGN PATENT DOCUMENTS

| | | |
|---|---|---|
| EP | 0556998 | 8/1993 |
| EP | 0689796 | 1/1996 |
| WO | 2006127486 | 11/2006 |

OTHER PUBLICATIONS

European search report for European application EP 08 16 2562 (2 pages).

(Continued)

*Primary Examiner* — Sameh Boles
(74) *Attorney, Agent, or Firm* — Maginot, Moore & Beck, LLP

(57) ABSTRACT

An instrument for attachment to a bone is disclosed herein. The instrument comprises a body portion providing a cutting guide. At least one hole extends through the body portion. The at least one hole includes a first portion configured to engage a handle. The at least one hole further includes a second portion configured to pass a bone engaging member having a shaft, such as a bone pin or a bone screw. The second portion of the at least one hole is not configured to pass the handle. The handle and the bone engaging member may be provided in various configurations. For example, the handle may be releasably connected to the shaft in a cannulated relationship. In another embodiment, the handle is integrally connected to the shaft.

5 Claims, 8 Drawing Sheets

(56) References Cited

U.S. PATENT DOCUMENTS

2004/0260301 A1* 12/2004 Lionberger et al. ............ 606/88
2006/0149245 A1* 7/2006 Sweeney ......................... 606/61
2006/0167465 A1* 7/2006 Lopez ........................... 606/104

OTHER PUBLICATIONS

European Search Report in corresponding European patent application (i.e., EP 10 17 8799) mailed Dec. 23, 2010, 2 pages.

* cited by examiner

ARRANGEMENT FOR SECURING INSTRUMENT TO BONE

FIELD

This invention relates to the field of orthopedics, and more particularly to instruments to be secured to a bone during orthopedic surgery.

BACKGROUND

Many orthopedic procedures involve tools or other instruments that need to be secured to the bone. One exemplary instrument is the cutting block which is used during orthopedic surgery to assist the surgeon in making bone cuts. Cutting blocks typically include slots or other guides that show the surgeon where the bone is to be cut. To ensure a proper cut, the cutting block must first be stabilized relative to the bone. With the cutting block stabilized, the cutting guides remain properly positioned and may be utilized by the surgeon to make a proper bone.

Different surgeons prefer different methods of stabilizing bone cutting instruments relative to the bone. For example, some surgeons prefer pin fixation to secure the cutting instrument. Other surgeons prefer handle fixation to secure the cutting instrument relative to the bone.

With pin fixation, a smooth or threaded fixation pin is inserted through a hole and into the bone. The pin typically includes a head that presses against the instrument and holds the instrument in place when the pin is inserted into the bone. With handle fixation, the cutting instrument includes one or more holes configured to receive handles. Once the handles are inserted into the holes, they extend from the instrument. The operating room team holds the handles firmly to stabilize the cutting instrument relative to the bone for the surgeon.

Surgical procedures, including orthopedic surgical procedures, are becoming increasingly less invasive. Smaller surgical instruments are desired for use in association with these less invasive surgical procedures. Accordingly, it would be advantageous to provide a cutting instrument for orthopedic surgeries where the stabilization features offered on the instrument consume only a minimum amount of space on the instrument. It would be of further advantage if the stabilization features on the cutting instrument continued to offer surgeons various options for stabilizing the cutting instrument relative to the bone. While it would be desirable to provide an instrument that includes one or more of these or other advantageous features as may be apparent to those reviewing this disclosure, the teachings disclosed herein extend to those embodiments which fall within the scope of the appended claims, regardless of whether they accomplish one or more of the above-mentioned advantages.

SUMMARY

An instrument for attachment to a bone is disclosed herein. The instrument comprises a body portion providing a cutting guide. At least one hole extends through the body portion. The at least one hole includes a first portion configured to engage a handle. The at least one hole further includes a second portion configured to pass a bone engaging member having a shaft, such as a bone pin or a bone screw. The second portion of the at least one hole is not configured to pass the handle.

In at least one embodiment, the first portion of the at least one hole and a shank of the handle include locking features designed to provide an interlock between the hole and the handle. For example, the locking features may comprise a particular shape defined by the first portion of the hole and a complimentary shape defined by the shank of the handle. In another embodiment, the locking features comprise threads in the first portion of the hole and complimentary threads on the shank of the handle.

The handle and the bone engaging member may be provided in various configurations. For example, the handle may be releasably connected to the shaft in a cannulated relationship. In another embodiment, the handle is integrally connected to the shaft. In yet another embodiment, the handle abuts the bone engaging member in the hole of the instrument.

The above described features and advantages, as well as others, will become more readily apparent to those of ordinary skill in the art by reference to the following detailed description and accompanying drawings.

DESCRIPTION

Figure 1:
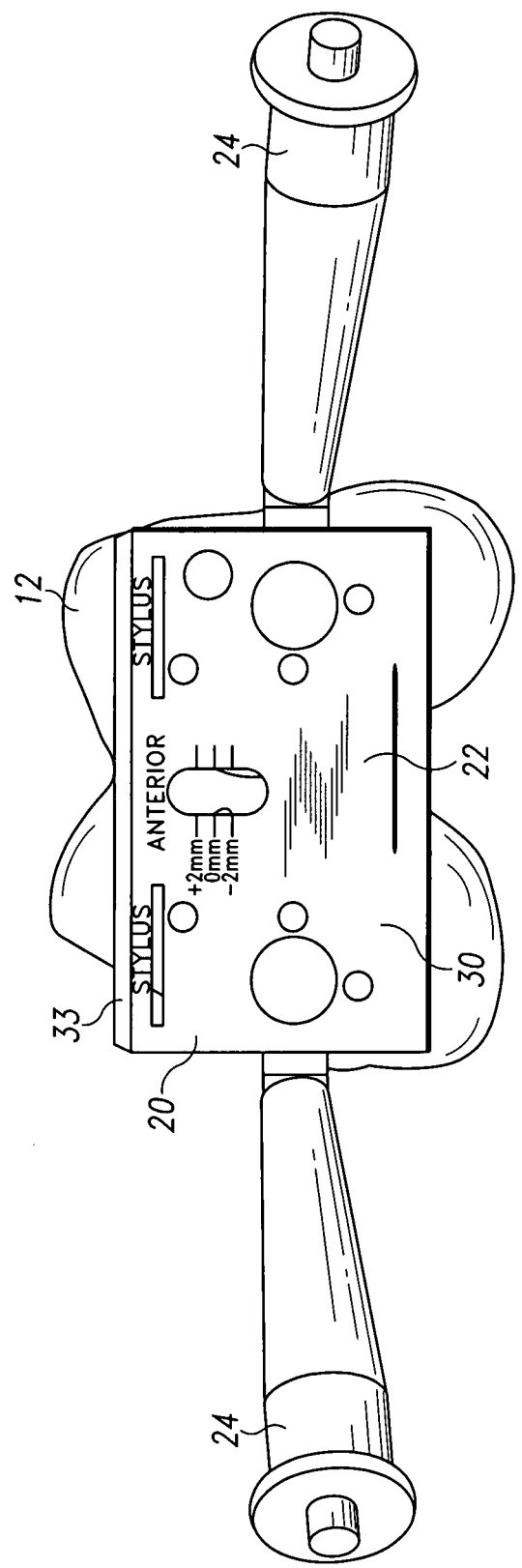
FIG. 1 shows a bone cutting instrument placed on the end of an exposed bone.

With reference to FIG. 1, a bone cutting instrument 20 is shown placed upon the end of an exposed femur 12 to be cut with the assistance of the instrument 20. The bone cutting instrument includes a cutting block 22 and securing members 24 used to secure the cutting block against the bone 12.

Figure 2:
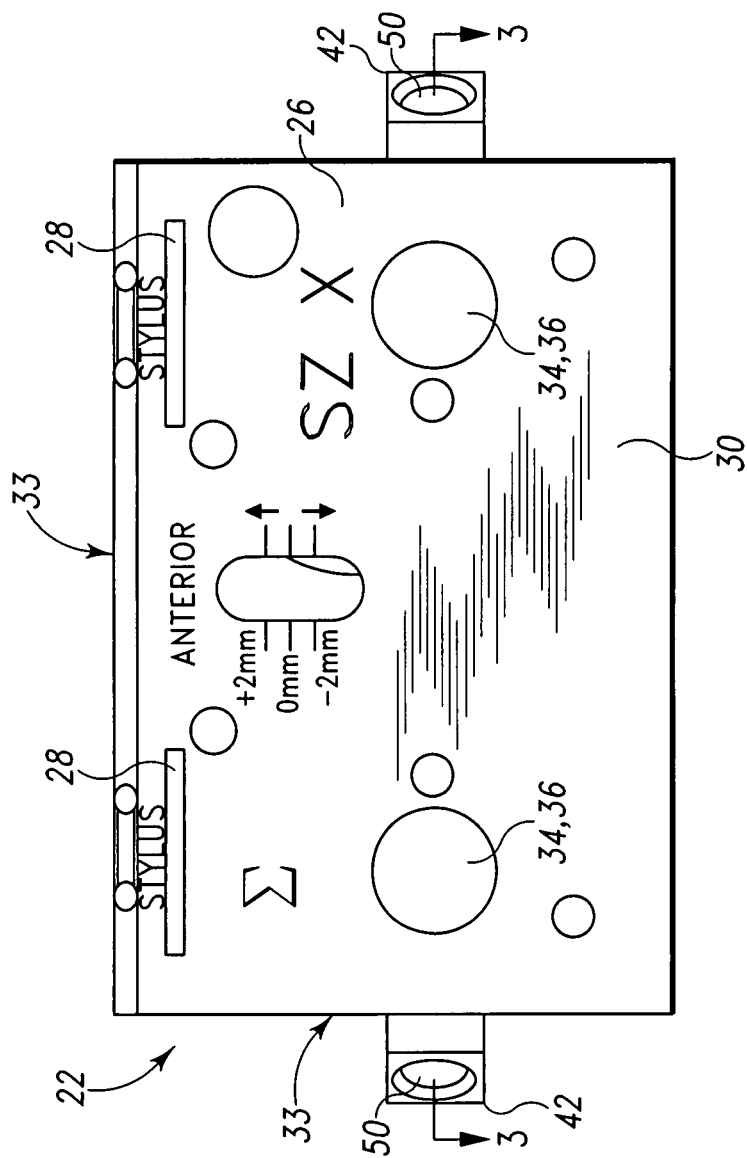
FIG. 2 shows the bone cutting instrument of FIG. 1 with the handles removed from the cutting block.
Figure 3:
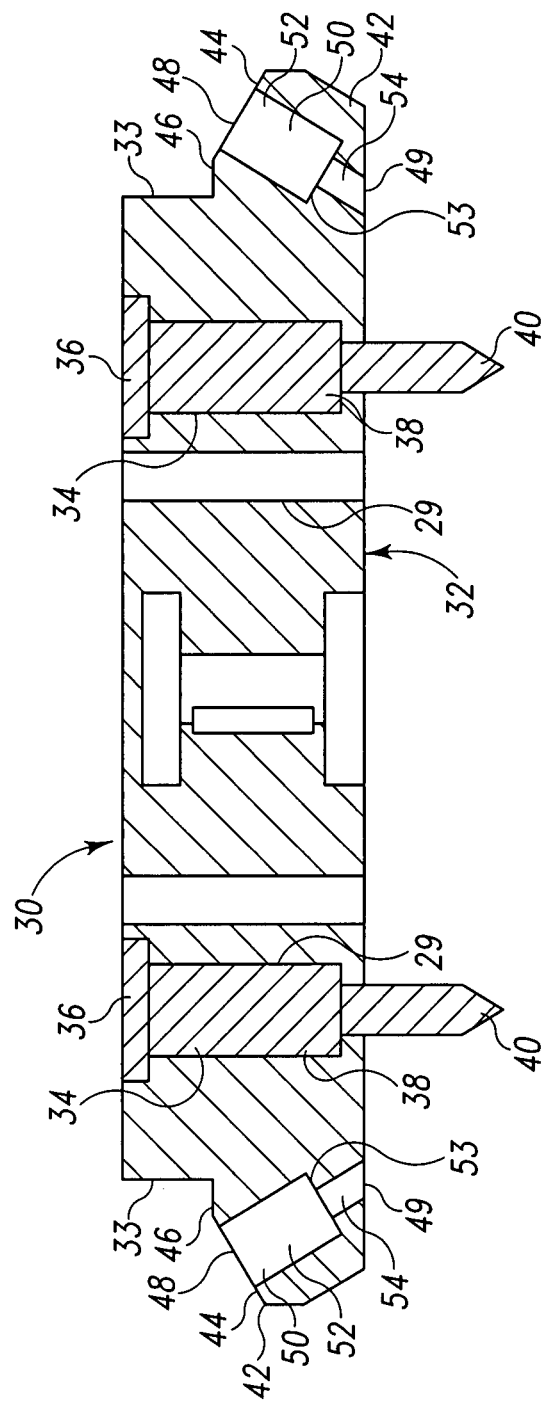
FIG. 3 shows a cross-sectional view of the bone cutting instrument of FIG. 2 along line III-III.

Turning now to FIGS. 2 and 3, the cutting block 22 is shown with the securing members 24 removed from a body portion 26 of the instrument 20. The body portion 26 is provided as a generally block-like structure including a first face 30, an opposite second face 32, and sidewalls 33 extending between the first face and the second face. The first face 30 may also be referred to herein as an upper face, and the second face 32 may be referred to as a lower face by virtue of the orientation of the cutting block 22 in the drawings. However, it will be recognized that the cutting block may be oriented in numerous different directions including those orientations where the first face 30 is actually in a lower position than the second face 32.

At least one cutting guide 28 extends through the body portion 26 of the cutting block 22 from the first face 30 to the second face 32. Each cutting guide 28 is generally provided as a rectangular slot that extends through the body portion 26 at a predetermined angle with respect to the face 30. Each slot is designed and dimensioned to receive a surgeon's cutting blade. When the second face 32 of the cutting block 22 is properly positioned on a bone surface, each cutting guide 28 provides a pilot to assist the surgeon in making proper cuts in the bone for a particular surgical procedure. In particular, when the surgeon's cutting blade is inserted into the cutting guide, the blade is properly oriented with respect to the bone such that an appropriate cut is made for the surgical procedure.

In addition to the cutting guides 28, the cutting block 22 includes a plurality of features designed to assist the surgeon and his or her team in stabilizing the block 22 on the bone during the cutting procedure. For example, the cutting block 22 includes pins 34 positioned in holes 29 in the cutting block 28 that extend from the first face 30 to the second face 32. Each pin 34 includes a head 36, a shaft portion 38 and a tip portion 40. The head 36 is initially provided apart from the first surface, but the head 36 is tapped by the surgeon toward the first face 30 in order to drive the tip portion 40 of the pin 34 outward from the second face 32 and into the bone.

Ears 42 are formed on opposing sidewalls of the cutting block 22. Each ear includes an upper surface 44 that extends from a shoulder 46 adjacent to the sidewall 33. The upper surface 44 is angled relative to the first face 30. An orifice 48 is formed in the upper surface 44 and the orifice 48 provides entry to a thru-hole 50 which extends down to the second surface 32 of the cutting block 22. Another orifice 49 to the thru-hole 50 is provided at the lower surface 32 of the cutting block. The thru-hole 50 is generally cylindrical and is defined by a center axis provided at an angle relative to the upper and lower faces 30, 32 of the cutting block. The cross-sectional shape of the thru-hole 50 is circular in the disclosed embodiment, however it will be recognized that in other embodiments the thru-hole 50 may have other cross-sectional shapes, as discussed in further detail below.

The thru-hole 50 includes a first portion 52 of a larger diameter and a second portion 54 of a smaller diameter. A shoulder 53 is formed in the thru-hole 50 at the intersection of the first portion 52 and the second portion 54. As explained in further detail below, the diameter of the first portion 52 is sufficiently large to receive the end portion or shank of a handle or other securing member for the cutting block. The first diameter portion 52 is also large enough to receive the head of a bone screw, bone pin, or other axial bone fixation device. However, the diameter of the second portion 54 will only pass the shaft of the bone fixation device, and neither a handle shank nor the head of the bone fixation device will pass through the second diameter portion. Accordingly, the head of a bone fixation device will remain in the first portion 52 while the shaft of the bone fixation device extends through the second portion 54, past the second face 32, and into the bone when the cutting block 22 is positioned against a bone.

Figure 4:
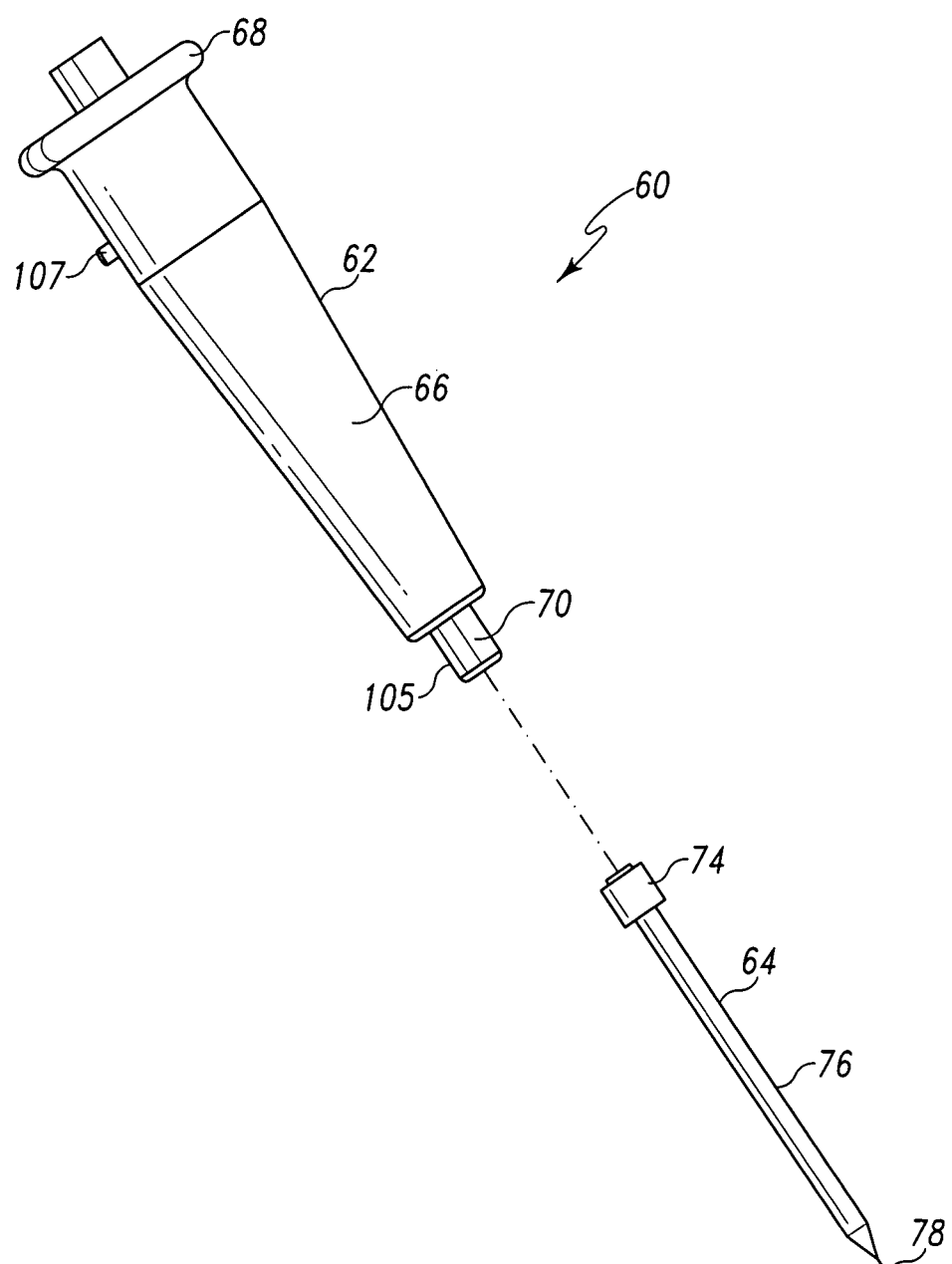
FIG. 4 shows one embodiment of a handle and bone fixation member for use with the cutting instrument of FIG. 2.

With reference now to FIG. 4, one embodiment of a securing arrangement 60 for a cutting block 22 is shown. The securing arrangement includes a handle 62 and a bone fixation device 64. The handle 62 includes a central portion 66 designed to be held in the hand of a surgical team member. The central portion is generally frusto-conical shaped with a disc portion 68 formed at the end of the handle 62. The disc portion provides a shoulder which allows a user to abut his or her finger against the disc portion when grasping the handle 62.

The handle 62 further includes a shank 70 on the opposite end of the handle from the disc portion 68. The shank is designed to fit into the first portion 52 of the thru-hole 50 in the cutting block 22. The shank 70 is provided as an end knob that is shaped complementary to the shape of the first portion 52 of the thru-hole 50. For example, if the first portion 52 of the thru-hole is cylindrical in shape with a circular cross-section, the end knob 70 is also cylindrical in shape with a circular cross-section. The end knob 70 is designed and dimensioned such that the complete end knob 70 fits into the first portion of the thru-hole 50.

In the embodiment of FIG. 4, a bone fixation device 64 in the form of a bone pin is shown in alignment with the handle 62. The bone pin 64 includes a head 74 and a shaft 76 with a sharp tip 78 on the end of the pin opposite the head 74. The bone pin is shown with a smooth surface on the shaft, but it will be recognized that the shaft could be provided with other surfaces, such as a threaded shaft. In any event, the bone pin 72 is designed and dimensioned for insertion in the thru-hole 50 of the cutting block 22.

When inserted in the thru-hole 50, the head 74 of the pin 64 is retained in the first portion 52 of the thru-hole 50 and abuts the shoulder 53 in the thru-hole 50. The shaft 76 of the pin extends through the lower face 32 of the cutting block 22. Accordingly, the tip 78 and shaft 76 of the pin 64 may be inserted into the bone when the cutting block is used in a surgical procedure to assist in securing the cutting block to the bone.

With the bone pin 64 in place, the surgeon may also choose to use the handle 62 for additional stabilization of the cutting block. To use the handle, the surgeon places the knob 70 in the first portion 52 of the thru-hole 50 of the cutting block 22 such that the knob 70 abuts the head 74 of the pin 64 in the thru-hole. Accordingly, with the arrangement of FIGS. 3 and 4, a single hole in the cutting block may be used in association with two securing members 24, including a bone fixation device 64 and also a handle 62.

Figures 5, 6, 8:
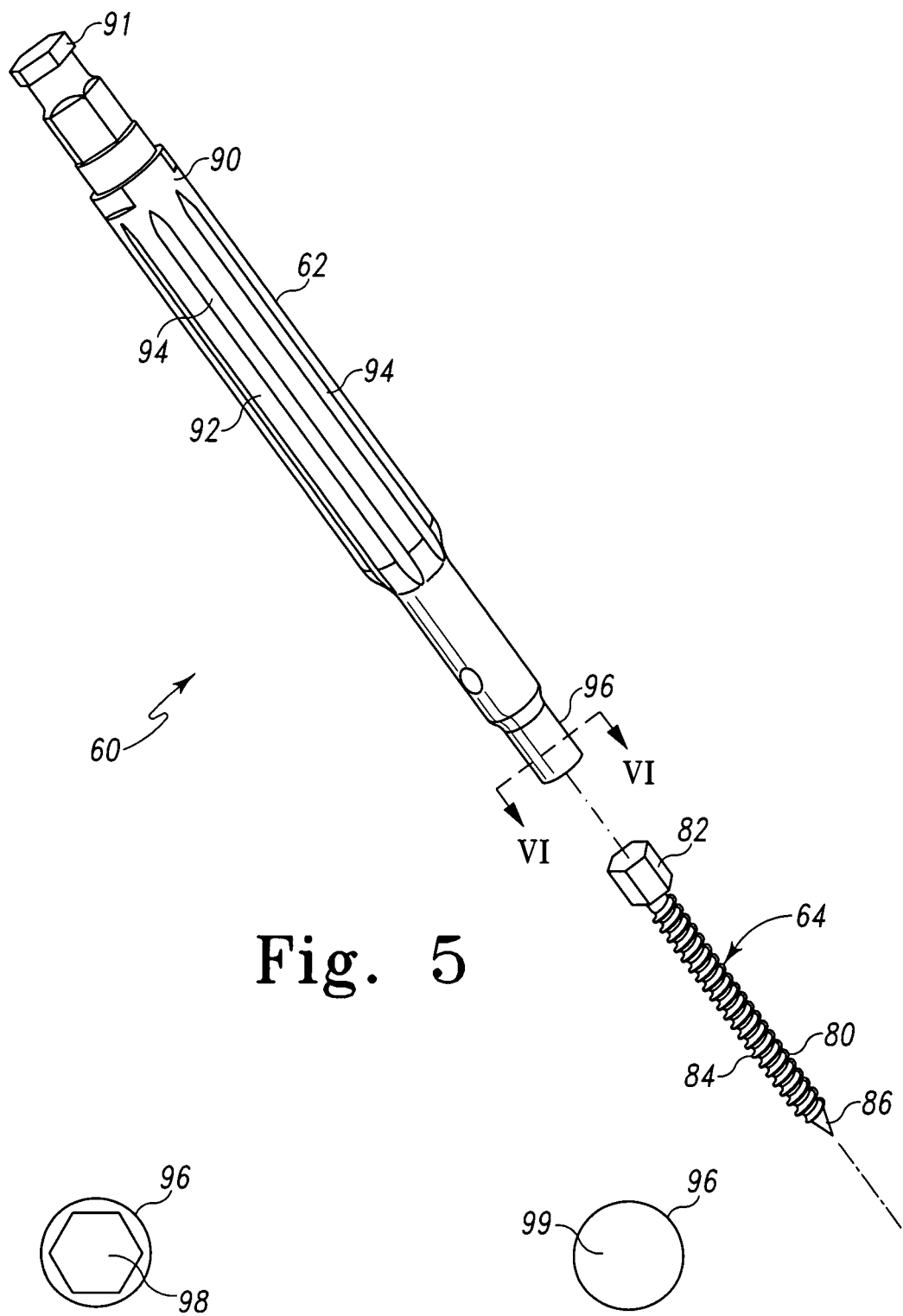
FIG. 5 shows an alternative embodiment of a handle and bone fixation member.
FIG. 6 shows a cross-sectional view of the handle of FIG. 5 along line VI-VI.
FIG. 8 shows an alternative cross-sectional view of the handle of FIG. 5 along line VI-VI.

FIGS. 5-10 show other embodiments of arrangements for securing instruments to the bone. In the embodiment of FIG. 5, an alternative embodiment of a handle 62 and bone fixation device 64 are shown. In this embodiment, the bone securing device 64 is a bone screw 80 including a hex-shaped head 82, a threaded shaft 84, and a tip 86. The handle 62 is a slotted handle 90 including a hex-shaped end portion 91 and a slotted central portion 92. The hex-shaped end portion 91 is configured to work in association with a wrench such that the handle 62 may be turned by the wrench. Elongated slots 94 are provided on the central portion 92 to assist the user in grasping the handle 90.

On the opposite end of the handle 90 from the hex-shaped end portion 91 is a circular shank 96. The shank 96 is designed with a circular outer circumference dimensioned to fit into the first portion 52 of the thru-hole 50 in the cutting block 22. In addition, the shank 96 is designed to interface with the head of the bone screw 80. In particular, as shown in FIG. 6, the end portion 96 of the handle 90 includes a hex-shaped cavity 98 that is complimentary to the hex-shaped head 82 on the bone screw 80. The hex shaped head 82 of the bone screw 80 is configured to fit within the complementary hex-shaped cavity 98 of the handle 90, providing a coaxial and cannulated arrangement between the handle 62 and the bone screw 80. With the head 82 of the bone screw 80 positioned in the cavity 98 of the handle 90, the bone screw 80 is releasably secured to the handle 90. In particular, rotation of the handle 90 about its axis allows the handle 90 to be used as a wrench to turn the bone screw. However, the when the handle 90 is pulled away from the bone screw 80 in an axial direction, the handle 90 is released from engagement with the bone screw 80.

Figure 7:
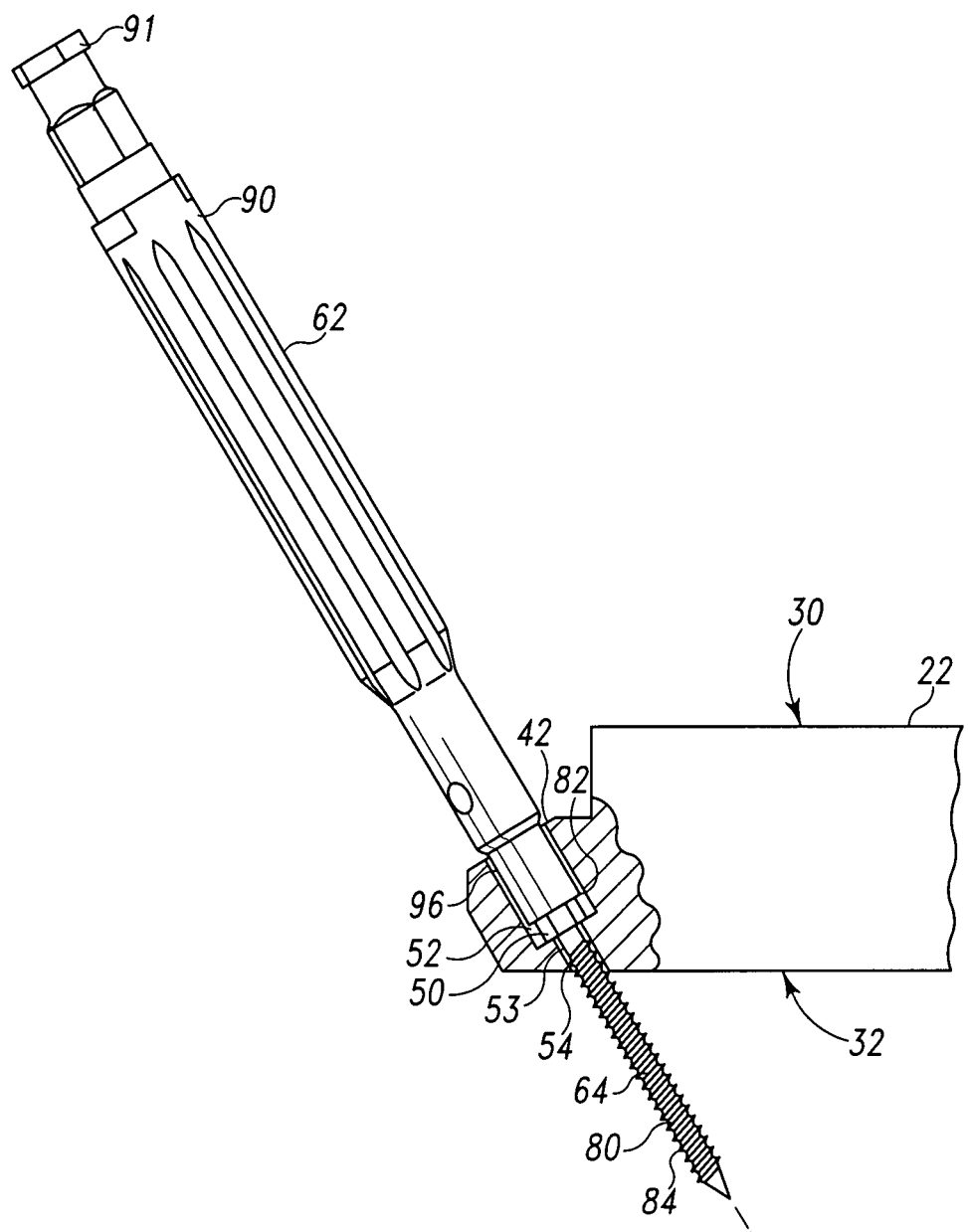
FIG. 7 shows the handle and bone fixation member of FIG. 5 positioned in a cutting instrument.

As shown in FIG. 7, both the handle 90 and the bone screw 80 may be inserted in the thru-hole 50. Insertion of the two parts many be accomplished with the bone screw 64 either separated from or in engagement with the handle 90. When the handle 90 and bone screw 64 are inserted into the thru-hole 50, the shank 96 of the handle 90 and the head 82 of the bone screw are retained in the first portion 52 of the thru-hole 50. The threaded shaft 84 of the bone screw 64 extends through the second portion of the thru-hole and past the lower face 32 of the cutting block. As mentioned previously, the cannulated relationship between the head 82 of the bone screw 64 and the cavity 98 of the handle 90, along with their complimentary hexagonal shapes, provide a lock between these parts. Accordingly, rotation of the handle 90 also results in rotation of the bone screw 64, and the handle 90 may be used to drive the bone screw 64 into the bone. It will be recognized that although a hexagonal shape is shown in FIGS. 5 and 6 as providing the locking engagement between the bone screw 64 and the handle 90, other shapes or locking arrangements may be provided between the handle 90 and the bone screw 80.

Although both the bone screw 80 and handle 90 are shown inserted into the thru-hole 50 of the cutting block 22 in FIG. 7, it will be appreciated that the surgeon may also choose to utilize only one of the two parts during a given surgical procedure. Thus, the bone screw 80 alone may be inserted into the thru-hole 50 of the cutting block 22 without the handle 90 in order to secure the cutting block 22 to the bone. Alternatively, the handle 90 may be used without the bone screw 80 to secure the cutting block 22 to the bone.

In an alternative embodiment to that shown in FIGS. 5-7, the shank 96 of the handle 90 does not include a cavity 98. Instead, as shown in FIG. 8, the shank 96 may be provided as a solid knob 99 designed to abut the head 82 of the bone screw 64. In this embodiment, the handle 90 and bone screw 80 are not coupled, but instead abut against one another in the first portion 52 of the cutting block's thru-hole 50. If the bone fixation device 64 is provided as a bone pin where the shaft is not threaded, such as that shown in FIG. 4, the handle may be used to drive the bone pin into the bone. In this embodiment, a surgeon may tap on the end 91 of the handle 90 with a mallet in order to drive the bone pin 80 into the bone until the head of the bone pin engages the shoulder 53 of the thru-hole 50.

Figure 9:
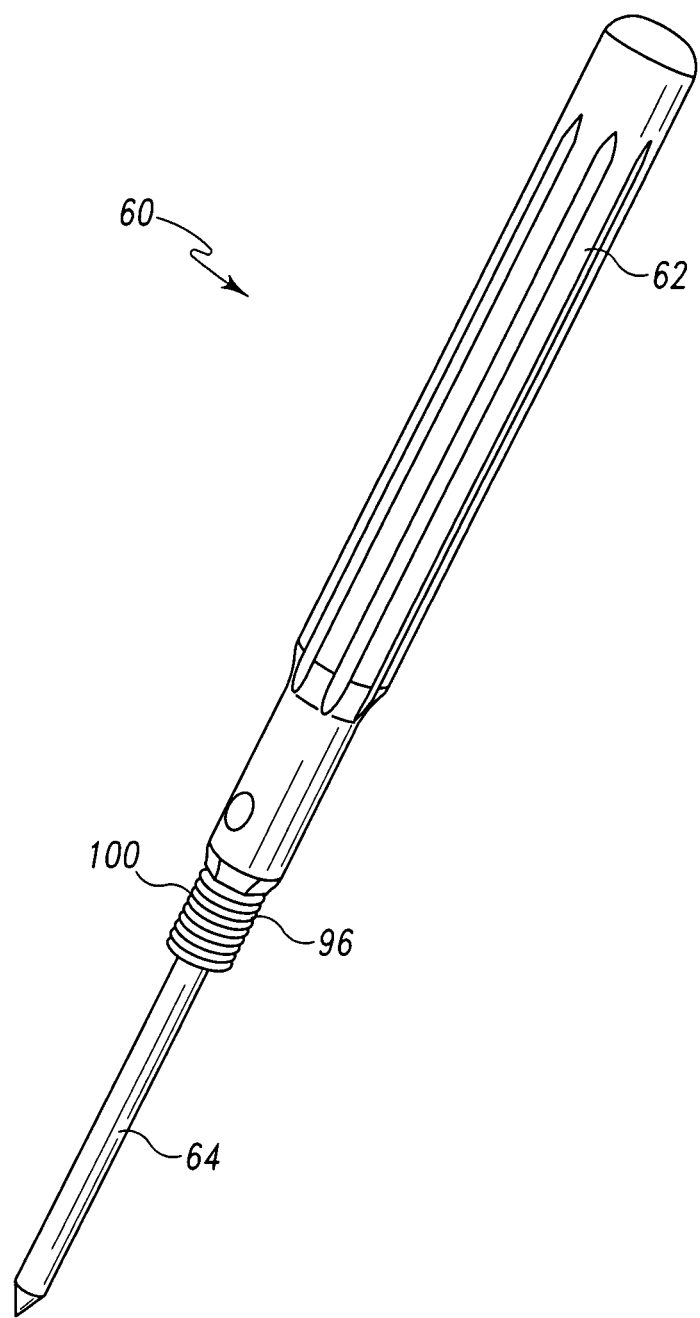
FIG. 9 shows yet another alternative embodiment of a handle and bone fixation member.

FIG. 9 shows yet another embodiment of a securing arrangement 60 for use with the bone cutting block 22. In this embodiment, the handle 62 is permanently attached to the bone fixation device 64, with the handle 62 and bone fixation device 64 formed as a single integral component. Although the bone fixation device is shown in FIG. 9 as being an unthreaded bone pin, it will be recognized that the bone fixation device could also be a threaded bone screw or other bone fixation device.

In the embodiment of FIG. 9, the shank 96 of the handle 62 includes a locking feature designed to secure the handle to the cutting block. In this embodiment, the locking feature is provided as threads 100 on the shank 96 of the handle 62. The threads 100 on the handle are designed to engage complimentary threads 101 provided in the first portion 52 of the thru-hole 50 of the cutting block 22. Engagement of the threads 100 and 101 provides an interlock between the handle 62 and the cutting block 22. Thus, when the threads 100 of the handle 62 engage the threads 101 of the cutting block 22, the handle 62 is secured to the cutting block 22 and can not be pulled away from the cutting block in the axial direction without rotating the handle to disengage the threads 100, 101.

Figure 10:
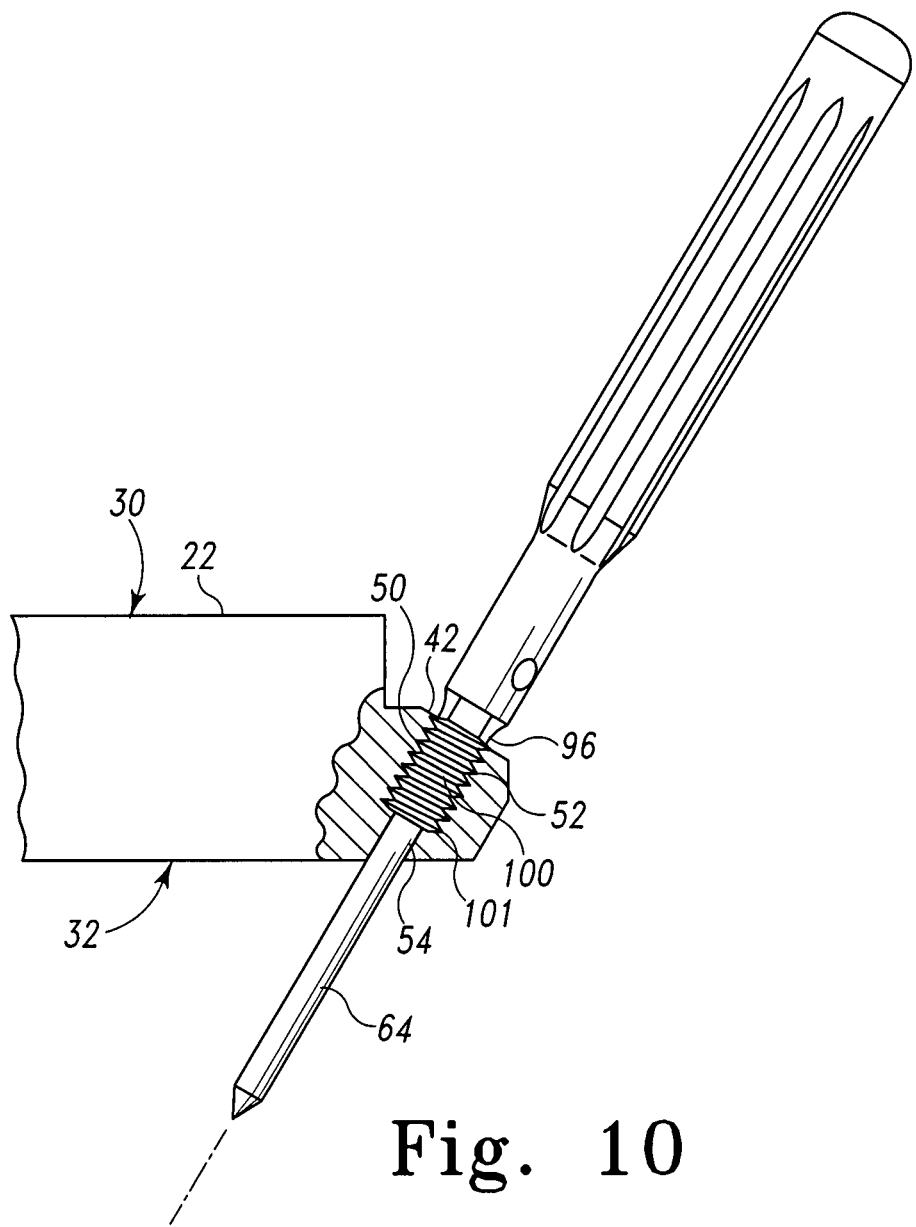
FIG. 10 shows the handle and bone fixation member of FIG. 9 positioned in a cutting instrument.

Although FIG. 10 shows one exemplary locking arrangement between the handle 62 and the cutting block 64, it will be appreciated that numerous other locking arrangements are possible. For example, returning again to FIG. 4, the knob 70 of the handle 62 may include locking balls 105 embedded in retaining cavities in the handle 62. These locking balls 105 are designed to engage a complimentary annular recess (not shown) in the first portion 52 of the thru-hole 50 when the knob 70 of the handle is fully inserted into the first portion 52 of the thru-hole 50. When the locking balls 105 engage the annular recess of the thru-hole 50, the handle 62 is locked in the thru-hole 50 in the axial direction. A button 107 provided on the opposite end of the handle from the knob 70 provides a release feature for the locking balls. In particular, the button 107 is provided in association with a release mechanism inside the handle such that depression of the button 107 allows the balls to be depressed further into the retaining cavities in the handle 62. When the locking balls 105 are depressed further into the retaining cavities, the handle may be inserted into or removed from the thru-hole. When the button is released, it returns to its outward position and the balls also are forced outward in the retaining cavities of the knob 70.

Figure 11:
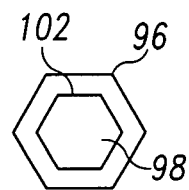
FIG. 11 shows an alternative cross-sectional view of the handle of FIG. 5 along line VI-VI.

Yet another exemplary arrangement where a locking feature is provided between the handle 62 and the cutting block 22 is shown in FIG. 11. In this embodiment, the locking feature is provided by the circumferential shape of the shank 96, such as hexagonal circumference 102 shown in FIG. 11. This circumference 102 is designed to engage a complimentary cross-sectional shape provided in the first portion 52 of the thru-hole 50 in the cutting block 22. When the hexagonal shank 96 of the handle 62 is inserted into the hexagonal first portion 52 of the thru-hole 50, the handle 62 is locked in the thru-hole and prevented from rotating. However, in this locking arrangement, the handle 62 may be easily removed from the thru-hole by pulling the handle 62 from the thru-hole in the axial direction, as no axial locking feature is provided with the embodiment of FIG. 11. Although a hexagonal circumference has been shown in FIG. 11, it will be recognized that numerous other shapes or arrangements are possible to provide locking features between the handle 62 and the cutting block 22.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An orthopedic surgery kit comprising:
    a surgical tool configured for placement against a bone, the surgical tool including at least one stabilization hole, the at least one stabilization hole including a first diameter portion and a second diameter portion;
    a handle member configured to engage the first diameter portion of the stabilization hole; and
    a bone-engaging pin including a first portion sized and shaped complementary to the second diameter portion of the at least one stabilization hole and a second portion configured to engage the first diameter portion.

2. The orthopedic surgery kit of claim 1 wherein the surgical tool further includes a cutting guide.

3. The orthopedic surgery kit of claim 1 wherein the handle member is configured for releasable connection to the pin.

4. The orthopedic surgery kit of claim 3 wherein the handle member includes a shank with a cavity and the pin includes a head configured to fit in the cavity.

5. The orthopedic surgery kit of claim 4 wherein the pin includes a threaded shaft portion.

* * * * *